United States Patent [19]

Kim et al.

[11] Patent Number: 5,091,384
[45] Date of Patent: Feb. 25, 1992

[54] ANTI-BACTERIAL QUINOLONE- AND NAPHTHYRIDONE-CARBOXYLIC ACID COMPOUNDS

[75] Inventors: Wan J. Kim; Myung H. Park; Jong H. Oh; Myung H. Jung; Bong J. Kim, all of Daejeon, Rep. of Korea

[73] Assignee: Korea Research Institute of Chemical Technology, Daejeon, Rep. of Korea

[21] Appl. No.: 599,225

[22] Filed: Oct. 19, 1990

[30] Foreign Application Priority Data

Oct. 23, 1989 [KR] Rep. of Korea .................... 89-15202

[51] Int. Cl.$^5$ ................. A61K 31/47; A61K 31/435; C07D 215/56; C07D 471/04
[52] U.S. Cl. .................................... 514/215; 514/300; 514/312; 540/580; 546/113; 546/123; 546/156
[58] Field of Search ............... 546/113, 123, 156; 540/580; 514/215, 300, 312

[56] References Cited

U.S. PATENT DOCUMENTS 4,988,709 1/1991 Ogata et al. ................. 546/156

Primary Examiner—Bernard Dentz
Attorney, Agent, or Firm—Finnegan, Henderson, Farabow, Garrett, and Dunner

[57] ABSTRACT

Quinolone compounds of the general formula

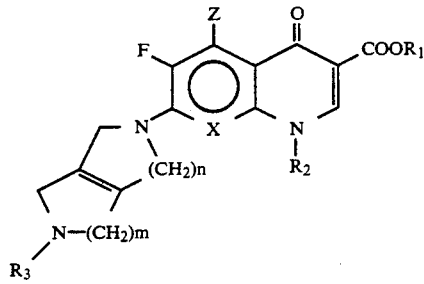

pharmaceutical compositions active against bacterial infections containing such compounds, processes for the manufacture of the quinolone compounds and the compositions and the use of the quinolone compounds for the manufacture of pharmaceutical compositions for the treatment of bacterial infections.

3 Claims, No Drawings

ANTI-BACTERIAL QUINOLONE- AND NAPHTHYRIDONE-CARBOXYLIC ACID COMPOUNDS

The present invention relates to new quinolone compounds of the following general formula I

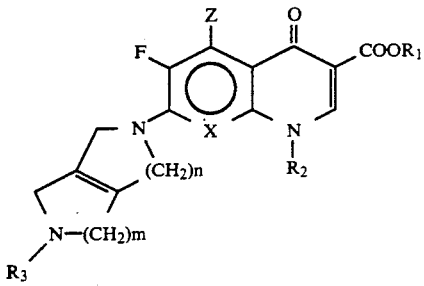

in which

X represents C—H, C—F or N,

Z represents hydrogen, halogen or amino, $R_1$ represents hydrogen or a pharmaceutically acceptable cation, $R_2$ represents alkyl, halogenated alkyl or hydroxyalkyl having 1 to 4 carbon atoms, vinyl, cycloalkyl having 3 to 6 carbon atoms or fluorophenyl, $R_3$ represents hydrogen, lower alkyl or formyl, m is an integer of 1 to 3, and n is 1 or 2, and, in case $R_1$ is hydrogen, pharmaceutically acceptable acid addition salts and the hydrates thereof.

These compounds have an excellent antibacterial activity and a broad antibacterial spectrum. The invention relates further to a process for their preparation.

If in the above formula I

Z is halogen, it may be e.g. chlorine or fluorine, preferably fluorine $R_2$ is alkyl having 1 to 4 carbon atoms, it may be e.g. methyl, ethyl, n-propyl, isopropyl or tert. butyl, preferably ethyl or tert. butyl;

halogenated alkyl having 1 to 4, preferably 2 to 4 carbon atoms, the halogen atom is preferably fluorine and a preferred substituent is 2-fluoroethyl;

hydroxyalkyl having 1 to 4, preferably 2 to 4 carbon atoms, a preferred substituent is 2-hydroxyethyl;

cycloalkyl, having 3 to 6 carbon atoms, it may be cyclopropyl, cyclobutyl, cyclopentyl or cyclohexyl, preferably cyclopropyl, fluorophenyl, it contains preferably 1 to 2 fluorine atoms, as for example 4-fluorophenyl or 2,4-difluorophenyl $R_3$ is lower alkyl, it is preferably an alkyl group with 1 to 4 carbon atoms, especially methyl or ethyl, $R_1$ is a pharmaceutically acceptable cation, it may be an alkali metal cation, preferably sodium or potassium, an alkaline earth metal cation, preferably calcium or magnesium and further ammonium or the cation of an organic base, such as e.g. tri- or tetra-$C_1$-$C_4$-alkylammonium, m is an integer of 1 to 3, it is preferably 1 to 2 and n is an integer of 1 to 2, it is preferably 1.

Especially preferred compounds of the formula I are those, in which X is CF or CH, Z is hydrogen, $R_1$ is hydrogen, $R_2$ is cyclopropyl, $R_3$ is hydrogen or $C_1$-$C_4$-alkyl, preferably methyl, and m and n each are the integer 1.

Since the first introduction of nalidixic acid, quinolone carboxylic acid antibacterial agents have been effectively used to cure urinary tract infections due to their antibacterial activity against many aerobic Gram negative bacteria. Among these quinolone antibacterial agents, especially norfloxacin, ciprofloxacin, and ofloxacin are being widely used in hospitals nowadays in a variety of indications.

However, whereas these existing quinolone antibacterial agents have a high antibacterial activity against Gram negative bacteria, these agents have a disadvantage due to their lower antibacterial activity against Gram positive bacteria, such as Staphylococcus spp. or Streptococcus spp.

As result of the effort to solve the antibacterial shortcomings of the existing quinolone antibiotics as stated above, the present invention was made.

It is an object of the present invention to provide the new quinolone compounds of the formula I having a much better and wider range of antibacterial activity than the existing quinolone antibacterial agents against Gram positive and Gram negative bacteria and having an excellent antibacterial activity against clinically important methicillin-resistant bacteria and bacteria resistant towards quinolones already used.

It is also an object of the present invention to provide a process for the preparation of the new quinolone compounds of the formula I and the pharmaceutically acceptable salts thereof.

The process for the preparation of the compounds of the general formula I comprises a₁) the step of condensing a compound of the general formula II

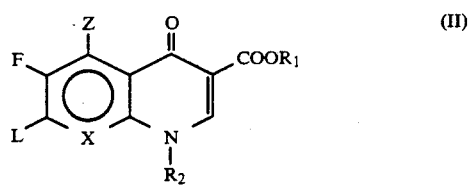

wherein X, Z, $R_1$ and $R_2$ are as defined above and L represents a leaving group, with a diazabicycloamine of the general formula III

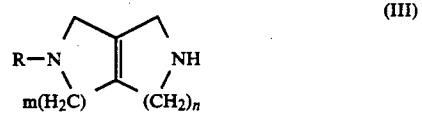

or its acid salt, wherein m and n are as defined above and

R represents hydrogen, lower alkyl or a protecting group, or a₂) the step of condensing a compound of the formula IIa

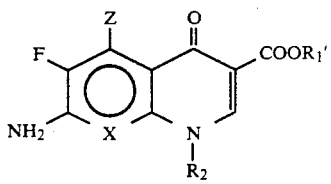

wherein Z, X and $R_2$ have the meaning given above and $R'_1$ stands for a protecting group,
with a compound of the formula IIIa

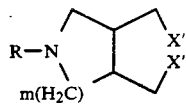

wherein R and m are as defined above and X' is a leaving group,
whereby a compound of the general formula IV

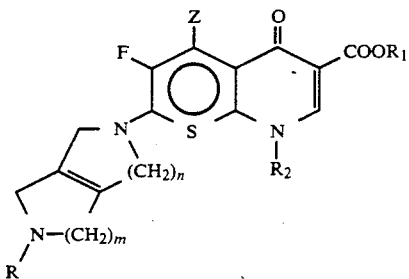

is obtained, in which Z, X, R, $R_1$, $R_2$, m and n are as defined above, but n is 1 for step $a_2$,
b) removing the protecting groups and
c) optionally replacing R=hydrogen by lower alkyl or formyl.

The leaving group L may be e.g. halogen, such as fluorine, chlorine or bromine, preferably fluorine, $C_1$-$C_4$-alkylsulfonyl, preferably ethylsulfonyl, or $C_1$-$C_4$-alkylsulfonyloxy.

As examples for the leaving group X' may be mentioned halogen, such as chlorine, bromine or iodine, preferably bromine.

If R stands for a protecting group, it may in principle be each N-protecting group known from literature, e.g. from peptide or β-lactam chemistry, which can easily be split off in conventional manner, i.e. by solvolysis, including hydrolysis, hydrogenolysis or by reduction after the inventive condensation.

As examples for protecting groups removable by solvolysis may be mentioned arylsulfonyl, such as p-toluenesulfonyl or phenylsulfonyl; or alkoxycarbonyl, such as ethoxy-, t-butoxy- or benzyloxycarbonyl. The removal may be carried out in well-known manner in an appropriate solvent in the presence of an acid, such as e.g. hydrochloric, hydrobromic, sulfuric, acetic, trifluoroacetic or formic acid, or in the presence of a base, such as e.g. sodium or potassium hydroxide, sodium or potassium carbonate or sodium acetate. The solvent may be water, or-if necessary-an organic solvent, as e.g. ethanol, dioxane or acetic acid, alone or in mixture with water.

Examples for protecting groups removable by hydrogenolysis are benzyl or substituted benzyl; or arylsulfonyl, such as p-toluenesulfonyl or phenylsulfonyl.

These groups can also be split off in customary manner known from literature under different conditions, e.g. in a hydrogen stream in an inert solvent in the presence of a catalyst, as e.g. platinum, palladium or Raney nickel; or with e.g. zink in acetic acid or methanol.

It is also possible to remove protecting groups such as e.g. toluenesulfonyl or phenylsulfonyl by reduction, as for instance by $NaAlH_2(OCH_2CH_2OCH_3)_2$.

Because compounds of the formula III wherein R is a protecting group are preferably obtained by a cyclization reaction which can be generalized as follows

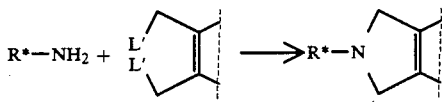

(R* = protecting group L' = leaving group)

protecting groups which can be introduced together with the nitrogen atom are therefore preferred, such as for instance arylsulfonyl, such as p-toluenesulfonyl, or alkylsulfonyl, such as methanesulfonyl (both introduced as the corresponding sulfonamide), alkoxycarbonyl (introduced as the corresponding urethane) or acetyl (introduced as acetamide), preferably the p-toluenesulfonyl group.

A protecting group $R'_1$ may be any easily removable carboxylic acid protecting group known from literature, preferably a $C_1$-$C_4$-alkyl group, especially ethyl, which can be removed in known manner e.g. under acidic or basic conditions.

As salts of the compound III salts with inorganic or organic acids can be used, such as e.g. hydrochloric acid, hydrobromic acid, formic acid or acetic acid, preferably hydrobromic acid.

In the above inventive process, the substituent $R_2$ is preferably ethyl, cyclopropyl, fluorophenyl or tertiary butyl.

The above reaction $a_1$ according to the present invention can be carried out advantageously in inert solvents such as e.g. acetonitrile, tetrahydrofuran, a lower alcohol, such as e.g. ethanol, chloroform, dimethylsulfoxide, dimethylformamide, pyridine, picoline or water, preferably acetonitrile.

In order to neutralize the acid produced during the reaction, the free amine of the general formula III can be used in excess. Alternatively, a carbonate or bicarbonate of an alkaline metal or alkaline earth metal, for example the sodium or potassium carbonate or bicarbonate, an organic base, as for example triethylamine, diisopropylethylamine, pyridine, picoline or especially DBU (1,8-diazabicyclo[5.4.0]undec-7-ene) can be used alone or as a mixture.

The above condensation is preferably carried out in a broad temperature interval, as for example between room temperature and 150° C., e.g. at reflux temperature of the used solvent, for about 1 to 10 hours.

If the variant $a_2$ is used, the reaction is also carried out in an inert solvent, such as e.g. dimethylformamide or acetonitrile, for example at room temperature for about 1 to 24 hours in the presence of a base, e.g. of anhydrous potassium carbonate.

The substituent $R_3$ in the compounds of the formula I can be introduced before or after the preparation of the compounds of formula IV. For example, monoalkylamines of the general formula III can be introduced by the above described processes and experimental conditions. Alternatively, by using methods known per se, for example the alkyl group can be introduced into compounds of the formula IV, wherein R is hydrogen, by the reaction with an alkyl halide, for example methyl or ethyl iodide, in an inert solvent, e.g. in dimethylformamide, in the presence of a base, e.g. of potassium carbonate. A methyl group can e.g. be introduced by the reaction with formaline, preferably about 36-37% aqueous formaline and formic acid, e.g. under reflux for about 2 to 6 hours. A formyl group can be introduced by reaction with formic acid in the presence of acetic anhydride. When R is a protecting group such as e.g. benzyl or tosyl, $R_3$ can only be introduced after removing this protecting group.

As starting materials of the present invention, the compounds of the general formula II are well known in the field of quinolone antibacterial agents and can be prepared according to the following references: J. P. Sanchez et al., J. Med. Chem. 31, 983 (1988), (2) J. M. Domagala et al., J. Med. Chem. 31, 503 (1988), (3) J. Mitsumoto et al., J. Heterocyclic Chem. 21, 673 (1984).

The manufacture of starting materials of the type IIIa is described below in the Preparations.

The diazabicycloamine compounds of the general formula III, as 3,7-diazabicyclo[3.3.0]oct-1(5)-ene) or 3,8-diazabicyclo[4.3.0]non-1(6)-ene or their acid salts, which are to be introduced onto the C-7 position of the quinolone compounds of formula II, are new compounds.

The compounds can for instance be prepared according to the following methods:

Preparation of 3,7-diazabicyclo[3.3.0]oct-1(5)-ene

Method A

The well known tetrakis(bromomethyl)ethylene [Reference: (1) A. C. Cope et al., J. Am. Chem. Soc., 80, 5499 (1958), (2) P. W. Le Quesne et al., J. Org. Chem., 40, 142 (1975)] is heated in a sealed tube with liquid ammonia and alcohol solvent. The above compound is obtained as the free amine.

Method B

Tetrakis(bromomethyl)ethylene is cyclized with p-toluene sulfonamide (or methanesulfonamide, urethane or acetamide) in the presence of a base and a polar solvent and then heated in the presence of a strong acid to remove the p-toluene sulfonyl group. The acid salt of the above compound is obtained.

Preparation of 3,8-diazabicyclo[4.3.0]non-1(6)-ene 3,4-Bis-bromomethyl-3-pyrroline is prepared by cyclization of tetrakis-(bromomethyl)ethylene with one equivalent of p-toluenesulfonamide. One of the two bromines is substituted by a cyanide group which is then reduced to the aminoethyl group. By cyclizing this compound in the presence of a base, nitrogen protected 3,8-diazabicyclo[4.3.0]non-1(6)-ene derivative is prepared.

Thereafter, the protecting group of this compound is removed in the presence of acid. Alternatively, the second protecting group, for example the benzyl group, is introduced into the secondary amine of this compound, the first protecting group is selectively removed in the presence of an acid and then the second protecting group is removed by hydrogenolysis under acidic conditions. Thus, the acid salt of the above compound is obtained. When it is treated with alkali, the free amine is obtained.

In the process of the present invention, each protecting group can—as already mentioned above—be removed by conventional methods e.g. by using an acid, as e.g. hydrobromic acid or alkali such as e.g. sodium hydroxide or potassium hydroxide, or by hydrogenolysis. Thus, N-protecting groups, such as toluenesulfonyl may preferably be removed by hydrobromic acid, for example 40% hydrobromic acid, in the presence of phenol under reflux conditions for several hours.

The hydrogenolysis to remove e.g. a benzyl group can also be carried out in usual manner, for example by using 10% Pd charcoal/hydrogen.

The present invention involves also the pharmaceutically acceptable acid addition salts and basic salts. The basic salts can be formed with an alkaline metal, as e.g. sodium or potassium, ammonium, an alkaline earth metal, as e.g. calcium or magnesium, or organic amines, as e.g. tri- or tetraalkyl ammonium. These salts may be obtained e.g. by treatment with the corresponding base, e.g. sodium or potassium hydroxide or with metal salts, e.g. with sodium or potassium carbonate.

The acid addition salts can be formed with appropriate organic acids or inorganic acids. Suitable acids for salt formation are, for example, hydrochloric acid, sulfuric acid, phosphoric acid, acetic acid, citric acid, lactic acid, boric acid, malonic acid, salicylic acid, malic acid, maleic acid, gluconic acid, fumaric acid, succinic acid, ascorbic acid and methanesulfonic acid, preferably hydrochloric acid. The above salts can be prepared in conventional manner by treatment of the above free base form of the compounds of the general formula I with an excess amount of acid which can form mono- or di-salts. Thus, the hydrochloride may, for example, be obtained by the treatment with 20% hydrochloric acid in isopropanol, or with isopropanol saturated with HCl-gas, or with concentrated hydrochloric acid in methanol, the formic acid salt e.g. by treatment with formic acid.

The compounds of the formula I may exist in their anhydrous form or as hydrates. Hydrates can be obtained during the isolation or by conventional methods.

The present invention involves also antibacterial compositions for oral or parenteral administration to human beings and animals, containing an effective amount of one or more of the quinolone compounds represented by the general formula I or salts thereof as active component, together with the usual pharmacologically acceptable excipients or diluents.

Pharmaceutical compositions which contain one or more compounds of the general formula I as the active compound can be prepared by mixing the compound(s) of the general formula I with one or more pharmacologically acceptable excipients or diluents, such as, for example, fillers, emulsifiers, lubricants, flavor-correcting agents, dyestuffs or buffer substances, and converting the mixture into a suitable galenical formulation form, such as, for example, tablets, dragees, capsules, granules, pellets, syrups, suspensions or a solution or suspension suitable for parenteral administration. Examples of commonly used excipients or diluents which may be mentioned are tragacanth, lactose, talc, starch, agar-agar, polyglycols, ethanol and water. Suspensions or solutions in water can preferably be used for parenteral administration. It is also possible to administer the active compounds as such, without excipients or diluents, in a suitable form for example in capsules. Suitable doses of the compounds of the general formula I are about 0.1 to 1.5 g/day, preferably 0.2 to 0.8 g/day, for an adult having a body weight of about 60 kg. The dose may vary depending e.g. upon the body weight, age or symptoms of the patient. Thus, individual doses or, in general, multiple doses may be administered, it being possible for the individual dose to contain the active compound in an amount of about 100 to 750 mg.

The products according to the invention can also be used in combination with other active compounds, for example from the series of penicillins, aminoglycosides, cephalosporins or other compounds which influence bacterial infections, such as, for example, antipyretic agents, analgesic agents or anti phlogistic agents.

The following examples and preparations illustrate the present invention without limiting the scope of the invention.

Preparations

Preparation 1

Preparation of 3,7-bis-p-toluenesulfonyl-3,7-diazabicyclo[3.3.0]oct-1(5)-ene 30 g of tetrakis (bromomethyl)ethylene and 30 g of p-toluene sulfonamide were dissolved in 400 ml of dimethylformamide. 150 g of potassium carbonate anhydride (or 50% sodium hydride 17 g) was added and then stirred at room temperature for 24 hours. Thereafter, this reaction mixture was distilled under vacuum to remove solvents. By adding 30 ml of water and 100 ml of ethylacetate, 17 g of the title compound was obtained as pale yellow powder (yield 50%).

Melting point: 250° C. (dec.).

$^1$H-NMR (DMSO-d$_6$, δ ppm): 7.65 (4H, d, J=8.08 Hz), 7.39 (4H, d, J=8.08 Hz), 3.94 (8H, s), 2.40 (6H, s).
EIMS: m/z 418 (M+, 1.3%), m/z 419 (M++1,1.2%).

Preparation 2

Preparation of 3,7-diazabicyclo[3.3.0]oct-1(5)-ene dihydrobromide 60 ml of 48% hydrobromic acid and 7 g of phenol were added to 10.8 g 3,7-bis-p-toluenesulfonyl-3,7-diazabicyclo [3.3.0]oct-1(5)-ene, prepared in Preparation 1. The mixture was refluxed for 4 hours and cooled to room temperature. The aqueous phase was separated by adding 100 ml of chloroform and 50 ml of water. The aqueous phase was washed with chloroform (100 ml×4) and decolorized with active carbon. The aqueous phase was concentrated under vacuum and the remained solid was washed with 1:1 methanol-ethyl ether solvent. 5 g of the title compound was obtained as white solid (yield 71%).

Melting point: 220° C. (dec.).

$^1$H-NMR (DMSO-D$_2$O, δ ppm): 4.06 (8H, s).
MS: m/z 110 (M+).

Preparation 3

Preparation of 3,7-diazabicyclo[3.3.0]oct-1(5)-ene 2.72 g of 3,7-diazabicyclo[3.3.0]oct-1(5)-ene dihydrobromide, prepared in Preparation 2, was added to 10 ml of 10% aqueous sodium hydroxide solution. The mixture was concentrated under reduced pressure to remove water, and then extracted with ether several times and concentrated. 1 g of the title compound was obtained (yield 90%).

$^1$H-NMR (D$_2$O, δ ppm): 4.02 (8H, s).
MS: m/z 110 (M+).

Preparation 4

Preparation of 3,7-diazabicyclo[3.3.0]oct-1(5)-ene 0.7 g of tetrakis (bromomethyl)ethylene was dissolved in 10 ml of methanol and 4 ml of liquid ammonia and sealed and heated in 180° C. oil bath for 8 hours. After cooling the reaction mixture to room temperature, ammonia was evaporated. The mixture was concentrated to remove methanol. 10 ml of absolute ethanol was added and the undissolved compound was filtered off to remove insoluble material. Ethanol was removed by vacuum distillation. 3 ml of 30% aqueous potassium hydroxide solution was added to the oil residue. The solution was extracted with tetrahydrofuran (THF, 5 ml×3) and the obtained extrates were combined and dried (Na$_2$SO$_4$), concentrated to give 60 mg of the title compound (yield 31%).

$^1$H-NMR (DMSO-d$_6$, δ ppm): 4.04 (8H, s,).
MS: m/z 110 (M+).

Preparation 5

Preparation of N-(p-toluenesulfonyl)-3,4-bis(bromomethyl)-3-pyrroline 19 g of tetrakis (bromomethyl)ethylene and 9 g of p-toluene sulfonamide were disolved in 220 ml of dimethylformamide. 30 g of anhydrous potassium carbonate was added and then stirred at room temperature for 20 hours. Thereafter solvent was removed by vacuum distillation. 50 ml of ethylacetate was added to obtain solid product, and solid product was purified by silica gel column chromatography. 12 g of the title compound was obtained (yield 60%).

Melting point: 170° C.

$^1$H-NMR (CDCl$_3$, δ ppm): 7.69 (2H, d, J=8.2 Hz), 7.33 (2H, d, J=8.2 Hz), 4.00 (4H, s), 3.15 (4H, s), 2.44 (s, 3H).

Preparation 6

Preparation of N-(p-toluenesulfonyl)-3-(bromomethyl)-4-(cyanomethyl)-3-pyrroline 10 g of N-(p-toluenesulfonyl)-3,4-bis(bromomethyl)-3-pyrroline, prepared in Preparation 5, was dissolved in 10 ml of dimethylsulfoxide (DMSO) and then heated in oil bath for 2 hours with refluxing. During the heating and refluxing, 1.5 g of sodium cyanide was added by small portion. The reaction mixture was cooled to room temperature and poured into ice water and then extracted with methylene chloride (200 ml×3). The extracts were combined, dried over Na$_2$SO$_4$ and concentrated. The residue was purified by silica gel column chromatography. 5 g of the title compound was obtained (yield 57%).

Melting point: 182° C.

$^1$H-NMR (CDCl$_3$, δ ppm): 7.71 (2H, d, J=8.2 Hz), 7.36 (2H, d, J=8.2 Hz), 4.01 (4H, s), 3.20 (2H, s), 3.06 (2H, s), 2.45 (3H, s).

Preparation 7

Preparation of
N-(p-toluenesulfonyl)-3-(aminoethyl)-4-(bromomethyl)-3-pyrroline 4 g of N-(p-toluenesulfonyl)-3-(bromomethyl)-4-(cyanomethyl)-3-pyrroline, prepared in Preparation 6, was dissolved in 100 ml of ethyl ether. The solution was slowly added to the suspension of 1 g of lithium aluminum hydride (LAH) in 20 ml of ethyl ether, and heated with refluxing for 3 hours. The reaction mixture was cooled by ice water. After adding 3 ml of water, it was stirred for 30 minutes and filtered off. The filtrate was concentrated. 2 g of the title compound was obtained (yield 49%).

Melting point: 185° C.

$^1$H-NMR (CDCl$_3$, δ ppm): 7.84 (2H, d, J=8.2 Hz), 7.46 (2H, d, J=8.2 Hz), 4.20 (2H, g, J=7 Hz), 4.06 (4H, s), 2.45 (3H, s), 2.26 (2H, t, J=7 Hz).

Preparation 8

Preparation of N$^8$-(p-toluenesulfonyl)-3,8-diazabicyclo[4.3.0]non-1(6)-ene 3.6 g of N$^1$-(p-toluenesulfonyl)-3-(aminoethyl)-4-(bromomethyl-3-pyrroline, prepared in Preparation 7, was dissolved in 30 ml of dimethylformamide. 5 g of anhydrous potassium carbonate was added to the solution and then stirred at room temperature for 18 hours. After concentrating the reaction mixture under reduced pressure to remove solvent, the mixture was extracted with methylene chloride (50 ml×3). After mixing the obtained extracts, it was washed with water and concentrated. 2.5 g of the title compound was obtained (yield 88%).

Melting point: 201° C.

$^1$H-NMR (CDCl$_3$, δ ppm): 7.80 (2H, d, J=8.2 Hz), 7.44 (2H, d, J=8.2 Hz), 4.05 (4H, s), 3.41 (2H, s), 2.92 (2H, t, J=5.8 HZ), 2.44 (2H, t, J=5.8 Hz).

Preparation 9

Preparation of
N$^3$-(benzyl)-N$^8$-(p-toluenesulfonyl)-3,8-diazabicyclo[4.3.0]non-1(6)-ene 1.8 g of N$^8$-(p-toluenesulfonyl)-3,8-diazabicyclo[4.3.0]non-1(6)-ene, prepared in preparation 8, was dissolved in 30 ml of methanol. 6 ml of 50% aqueous sodium hydroxide solution and 1.5 ml of benzyl bromide were added to the solution and stirred at room temperature for 5 hours. The reaction mixture was concentrated under reduced pressure to remove methanol and then extracted with methylene chloride (30 ml×3). It was dried (Na$_2$SO$_4$) and concentrated and then dried under reduced pressure. 2 g of the title compound was obtained (yield 85%).

Melting point: 196° C.

$^1$H-NMR (CDCl$_3$, δ ppm): 7.80 (2H, d, J=8.2 Hz), 7.44 (2H, d, J=8.2 Hz), 7.28 (5H, br. s), 4.01 (4H, s), 3.56 (2H, s), 3.40 (2H, s), 2.90 (2H, d, J=5.8 Hz), 2.22 (2H, t, J=5.8 Hz).

Preparation 10

Preparation of
N$^3$-(benzyl)-3,8-diazabicylclo[4.3.0]non-1(6)-ene hydrobromide 2 g of N$^3$-(benzyl)-N$^8$-(p-toluenesulfonyl)-3,8-diazabicyclo[4.3.0]non-1(6)-ene, prepared in Preparation 9, was suspended in 15 ml of 48% hydrobromic acid and 1.5 g of phenol, and the reaction mixture was refluxed for 3 hours. After cooling the reaction mixture, 20 ml of water was added the mixture was washed with chloroform (50 ml×3). The aqueous phase was taken and decolorized by active carbon. The aqueous phase was concentrated under reduced pressure and thus resulting solid was washed with 1:1 methanol-ethylether solvent. 1.5 g of the title compound was obtained (yield 98%).

Melting point: 205° C.(dec.)

$^1$H-NMR (CDCl$_3$, δ ppm): 7.29 (5H, br. s), 4.00 (4H, s), 3.55 (2H, s), 3.38 (2H, s), 2.91 (2H, d, J=5.8 Hz), 2.24 (2H, t, J=5.8 Hz).

Preparation 11

Preparation of 3,8-diazabicyclo[4.3.0]non-1(6)-ene dihydrobromide 1.5 g of N$^8$-(p-toluenesulfonyl)-3,8-diazabicyclo[4.3.0]non-1(6)-ene, prepared in Preparation 8, was suspended in 15 ml of 48% hydrobromic acid and 2 g of phenol, and the reaction mixture was refluxed for 4 hours. After cooling the reaction mixture, 20 ml of water was added. The mixture was washed with chloroform (40 ml×3). The aqueous phase was taken and decolorized by active carbon. The aqueous phase was concentrated under reduced pressure and thus resulting solid was washed with 1:1 methanol-ethylether solvent. 0.9 g of the title compound was obtained (yield 98%).

Melting point: 225°-227° C.(dec.).

Preparation 12

Preparation of 3,8-diazabicyclo[4.3.0]non-1(6)-ene dihydrobromide 0.7 g of N$^3$-(benzyl)-3,8-diazabicyclo[4.3.0]non-1(6)-ene hydrobromide, prepared in Preparation 10, was dissolved in 20 ml of 5% aqueous acetic acid solution. 0.5 g of 10% palladium chracoal in this solution was suspended and the reaction mixture was refluxed under the hydrogen stream for 7 hours. The solid was filtered off. The filtrate was concentrated under reduced pressure and dissolved in 10 ml of 48% bromic acid. By concentrating the solution under reduced pressure again, 0.5 g of the title compound was obtained (yield 73%).

Melting point: 225°∼227° C.(dec.).

Preparation 13

Preparation of
3-methyl-3,7-diazabicyclo[3.3.0]oct-1(5)-ene dihydrobromide 3,7-Diazabicyclo[3.3.0]oct-1(5)-ene dihydrobromide (0.81 g) which was prepared in Preparation 2 was dissolved in water (10 ml). To this solution 35% formaline (0.3 ml) and formic acid (10 ml) were added and refluxed for 4 hours. The solvents were distilled off and the resulting solid was washed with isopropylalcohol (20 ml) and ethylether (20 ml) to give the title compound (0.81 g, yield 94%).

Melting point: 185°∼187° C.(dec.).

Preparation 14

Preparation of 3-ethyl-3,7-diazabicyclo[3.3.0]oct-1(5)-ene dihydrobromide

To a solution of 1-p-toluene sulfonyl-3,4-bis (bromomethyl)-3-pyrroline (3.41 g) in acetonitrile (43 ml), 0.73 ml of 70% ethylamine and anhydrous potassium carbonate (8 g) were added and stirred at room temperature for one hour.

The solid was filtered off and the filtrate was purified by silicagel column chromatography ($CHCl_3$-MeOH) to give 3-ethyl-7-p-toluene sulfonyl-3,7-diazabicyclo [3.3.0]oct-1(5)-ene (0.95 g, yield 39%). 0.9 g of this compound was hydrolysized in 20 ml of 48% hydrobromic acid with 1 g of phenol. The hydrolysate was washed with chloroform (30 ml×3) and decolorized with active carbon. The solvent was concentrated and washed with ethanol to give the titled compound (0.57 g, yield 62%).

MS m/z (rel. int. %): M+138 (32), 123 (20), 109 (60), 108 (100).

EXAMPLES

Example 1

Preparation of 1-cyclopropyl-7-[3,7-diazabicyclo[3.3.0]oct-1(5)-en-3-yl]-6,8-difluoro-1,4-dihydro-4-oxoquinoline-3-carboxylic acid (KR-10679)

0.4 g of 1-cyclopropyl-6,7,8-trifluoro-1,4-dihydro-4-oxoquinoline-3-carboxylic acid, 0.8 g of 3,7-diazabicyclo[3.3.0]oct-1(5)-ene dihydrobromide and 0.8 ml of 1,8-diazabicyclo[5.4.0] undec-7-ene (DBU) were suspended in 30 ml of acetonitrile and the suspension was refluxed in 100° C. oil bath for 8 hours. The reaction mixture was kept overnight at room temperature. The produced precipitate was filtered and washed with methanol. 0.35 g of the title compound was obtained (yield 67%)

Melting point: 220°~222° C.(dec.).

$^1$H-NMR ($CDCl_3$+$CD_3COOD$, δ ppm): 8.81 (1H, s), 7.87 (1H, dd, J=14.2, 1.8 Hz), 4.69 (4H, s), 4.24 (4H, s), 4.01 (1H, m), 1.23 (4H, m).

Example 2

Preparation of 5-amino-1-cyclopropyl-7-[3,7-diazabicyclo[3.3.0]oct-1(5)-en-3-yl]-6,8-difluoro-1,4-dihydro-4-oxoquinoline-3-carboxylic acid (KR-10747)

0.4 g of 5-amino-1-cyclopropyl-6,7,8-trifluoro-1,4-dihydro-4-oxoquinoline-3-carboxylic acid, 0.8 g of 3,7-diazabicyclo[3.3.0]oct-1(5)-ene dihydrobromide and 0.6 ml of 1,8-diazabicyclo[5.4.0] undec-7-ene (DBU) were suspended in 40 ml of acetonitrile and the suspension was refluxed in 100° C. oil bath for 7 hours. The reaction mixture was kept overnight at room temperature. The produced precipitate was filtered and washed with methanol. 0.3 g of the titled compound was obtained (yield 57%).

Melting point: 220°~225° C.(dec.).

$^1$H-NMR ($CDCl_3$+$CD_3COOD$, δ ppm): 8.69 (1H, s), 4.65 (4H, s), 4.24 (4H, s), 3.91 (1H, m), 1.18 (4H, m).

Example 3

Preparation of 1-cyclopropyl-7-[7-methyl-3,7-diazabicyclo[3.3.0]oct-1(5)-en-3-yl]-6,8-difluoro-1,4-dihydro-4-oxoquinoline-3-carboxylic acid hydrochloride (KR-10755)

0.1 g of 1-cyclopropyl-7-[3,7-diazabicyclo[3.3.0]oct-1(5)-en-3-yl]-6,8-difluoro-1,4-dihydro-4-oxoquinoline-3-carboxylic acid, prepared in Example 1, was dissolved in the mixture of 36% aqueous formaline solution 1 ml and 1.5 ml of formic acid. The reaction mixture was refluxed at 120° C. for 2 hours and concentrated under reduced pressure to remove solvent. 1 ml of isopropyl alcohol and 1 ml of 20% hydrochloric acid was added to the reaction mixture and then refluxed for 1 hour. It was concentrated under reduced pressure to remove the solvent and washed with methanol-ethylether (1:1) solvent. 0.082 g of the title compound was obtained (yield 78%).

Melting point: 210°~213° C.(dec.).

$^1$H-NMR ($CDCl_3$+$CD_3COOD$, δ ppm): 8.82 (1H, s), 7.85 (1H, d, J=14.3 Hz), 4.83 (2H, m), 4.67 (4H, br. s), 3.98 (m, 1H), 3.89 (2H, m), 3.16 (3H, s), 1.24 (4H, m).

Example 4

Preparation of 1-cyclopropyl-7-[3,7-diazabicyclo[3.3.0]oct-1(5)-en-3-yl]-5,6,8-trifluoro-1,4-dihydro-4-oxoquinoline-3-carboxylic acid (KR-10758)

0.6 g of 1-cyclopropyl-5,6,7,8-tetrafluoro-1,4-dihydro-4-oxoquinoline-3-carboxylic acid, 1,2 g of 3,7-diazabicyclo[3.3.0]oct-1(5)-ene dihydrobromide and 1.3 ml of 1,8diazabicyclo[5.4.0]undec-7-ene (DBU) were suspended in 32 ml of acetonitrile and the suspension was refluxed for 10 hours. The reaction mixture was kept overnight at room temperature. The produced precipitate was filtered and washed with ethanol. 0.58 g of the titled compound was obtained (yield 74%).

Melting point: 226°~228° C.(dec.).

$^1$H-NMR ($CDCl_3$+$CD_3COOD$, δ ppm): 8.71 (1H, s), 4.68 (4H, s), 4.18 (4H, s), 4.00 (1H, m), 1.22 (4H, m).

Example 5

Preparation of 1-cyclopropyl-7-[7-methyl-3,7-diazabicyclo[3.3.0]oct-1(5)-en-3-yl]-5,6,8-trifluoro-1,4-dihydro-4-oxoquinoline-3-carboxylic acid hydrochloride 0.15 g of 1-cyclopropyl-7-[3,7-diazabicyclo[3.3.0]oct-1(5)-en-3-yl-5,6,8-trifluoro-1,4-dihydro-4-oxoquinoline-3-carboxylic acid, prepared in Example 4, was dissolved in the mixture of 1.2 ml of 36% aqueous formaline solution and 2 ml of formic acid. Following processes were accomplished by the same method as Example 3. 0.14 g of the title compound was obtained (yield 90%).

Melting point: 230°~233° C.(dec.).

$^1$H-NMR ($CDCl_3$+$CD_3COOD$, δ ppm): 8.86 (1H, s), 4.73 (2H, s), 4.70 (4H, s), 4.31 (2H, m), 4.02 (1H, m), 3.19 (3H, m), 1.24 (4H, m).

Example 6

Preparation of 1-cyclopropyl-6-fluoro-7-[3,7-diazabicyclo[3.3.0]oct-1(5)-en-3-yl]-4-oxo-1,8-naphtylidine-3-carboxylic acid (KR-10797)

0.5 g of 3,7-diazabicyclo[3.3.0] oct-1(5)-ene dihydrobromide and 0.5 g of 1,8-diazabicyclo[5.4.0] undec- 7-ene (DBU) were suspended in 30 ml of acetonitrile, and the suspension was refluxed. During the refluxing, 0.25 g of 1-cyclopropyl-7-ethylsulfonyl-6-fluoro-4-oxo-1,8-naphthylidine-3-carboxylic acid was added by small amount. The reaction mixture was refluxed for additional one hour and kept overnight at room temperature. The produced precipitate was filtered and washed with ethanol-ethylether (1:1) solvent. 0.22 g of the title compound was obtained (yield 84%).

Melting point: 267° C. (dec.).

$^1$H-NMR (DMSO-d$_6$, δ ppm): 8.87 (1H, s), 8.08 (1H, d, J=12.5 Hz), 4.60 (4H, s), 4.21 (4H, s), 3.96 (H, m), 1.26 (4H, m).

Example 7

Preparation of 1-cyclopropyl-6,8-difluoro-7-{3,8-diazabicyclo [4.3.0] non-1(6)-en-3-yl}-1,4-dihydro-4-oxoquinoline-3-carboxylic acid hydrobromide 0.3 g of 1-cyclopropyl-6,7,8-trifluoro-1,4-dihydro-4-oxoquinoline-3-carboxylic acid and 0.42 g of 8-p-toluenesulfonyl-3,8-diazabicyclo[4.3.0]non-1(6)-ene were dissolved in 20 ml of acetonitrile. 0.3 ml of 1,8-diazabicyclo[5.4.0]undec-7-ene (DBU) were added and then refluxed for 5 hours. The reaction mixture was kept overnight at room temperature. The produced precipitate was filtered and suspended in the mixture of 20 ml of 40% hydrobromic acid and 1 g of phenol. The suspension was refluxed for 5 hours. The reaction mixture was cooled to room temperature and then washed five times with methylene chloride (30 ml×5). The aqueous phase was concentrated under reduced pressure and washed with the ethanol-ethylether (1:1) solvent. 0.34 g of the title compound was obtained (yield 68%).

Melting point: 287°~291° C.(dec.)

$^1$H-NMR (CDCl$_3$+CD$_3$COOD, δ ppm): 8.80 (1H, s), 7.88 (1H, d, J=14 Hz), 4.10 (4H, s), 4.00 (1H, m), 3.40 (2H, s, br), 2.94 (2H, t, J=5.8 Hz), 2.31 (2H, t, J=5.8 Hz), 1.25 (4H, m).

Example 8

Preparation of 1-cyclopropyl-6,8-difluoro-7-{3,8-diazabicyclo[4.3.0] non-1(6)-en-8-yl}-1,4-dihydro-4-oxoquinoline-3-carboxylic acid 0.3 g of 1-cyclopropyl-6,7,8-trifluoro-1,4-dihydro-4-oxoquinoline-3-carboxylic acid and 0.6 g of 3-benzyl-3,8-diazabicyclo[4.3.0] non-1(6)-ene hydrobromide were suspended in 30 ml of acetonitrile. 0.6 ml of 1,8-diazabicyclo[5.4.0] undec-7-ene (DBU) was added to the suspension. The reaction mixture was refluxed for 5 hours and then kept overnight at room temperature. The produced precipitate was filtered and dissolved in 30 ml of 5% acetic acid in ethanol. After adding 0.5 g of 10% palladium charcoal, the reaction mixture was stirred under the hydrogen stream for 6 hours and then filtered. The filtrate was concentrated under reduced pressure. 0.25 g of the title compound was obtained (yield 61%).

Melting point: 270° C.(dec.).

$^1$H-NMR (CDCl$_3$+CD$_3$COOD, δ ppm) : 8.84 (1H, s), 7.89 (1H, d, J=14 Hz), 4.60 (4H, s), 4.02 (1H, m), 3.41 (2H, s), 2.94 (2H, t, J=5.8 Hz), 2.27 (2H, t, J=5.8 Hz), 1.27 (4H, m).

Example 9

Preparation of 1-cyclopropyl-6,8-difluoro-7-[3,7-diazabicyclo [3.3.0] oct-1(5)-en-3-yl]-1,4-dihydro-4-oxoquinoline-3-carboxylic acid hydrobromide 0.33 g of the 7-amino-1-cyclopropyl-6,8-difluoro-1,4-dihydro-4-oxoquinoline-3-carboxylic acid ethyl ester, 0.41 g of N-(p-toluenesulfonyl)-3,4-bis(bromomethyl)3-pyrroline and 0.5 g of anhydrous potassium carbonate were suspended in 20 ml of dimethylformamide and the suspension was stirred at room temperature for 24 hours. After adding 100 ml of water, the produced precipitate was filtered.

The precipitate was suspended in 20 ml of 47% hydrobromic acid and 0.5 g of phenol and the reaction mixture was refluxed for 5 hours. After cooling the reaction mixture to the room temperature 20 ml of water was added again. The mixture was extracted with chloroform several times. The aqueous phase was decolorized with active carbon and concentrated under reduced pressure. 0.3 g of the title compound was obtained (yield 75%).

Melting point: 280°~282° C.(dec.)

Example 10

Preparation of 1-cyclopropyl-7-[3,7-diazabicyclo[3.3.0]oct-1(5)-en-3-yl]-6,8-difluoro-1,4-dihydro-4-oxoquinoline-3-carboxylic acid (KR-10679)

0.28 g of 1-cyclopropyl-6,7,8-trifluoro-1,4-dihydro-4-oxoquinoline-3-carboxylic acid, 0.16 g of 3,7-diazabicyclo-[3.3.0]oct-1(5)-ene and 0.3 ml of 1,8-diazabicyclo[5.4.0] undec-7-ene (DBU) were suspended in 20 ml of acetonitrile and refluxed in 100° C. oil bath for 5 hours. The reaction mixture was kept overnight at room temperature. The produced precipitate was filtered and was washed with ethanol-ethylether (1:1) solvent. 0.3 g of the title compound was obtained (yield 80%).

Melting point: 220°~223° C.(dec.)

Example 11

Preparation of 1-cyclopropyl-7-[3,7-diazabicyclo[3.3.0] oct-1(5)-en-3-yl]-6,8-difluoro-1,4-dihydro-4-oxoquinoline-3-carboxylic acid (KR-10679)

The suspension of 1-cyclopropyl-6,7,8-trifluoro-1,4-dihydro-4-oxoquinoline-3-carboxylic acid (14.7 g), 3,7-diazabicyclo[3.3.0] oct-1(5)-ene dihydrobromide (14.1 g) and diisopropyl-ethylamine (45 ml) in acetonitrile (1 l) was refluxed for 5 hours. The reaction mixture was cooled to room temperature and the produced precipitate was filtered and then washed with acetonitrile (200 ml) and water (200 ml) successively. Vacuum drying gave the title compound (16.6 g, yield 85%).

mp: 220°~222° C.(dec.)

Example 12

Preparation of 1-cyclopropyl-7-[3,7-diazabicyclo[3.3.0] oct-1(5) -en-3-yl]-6,8-difluoro-1,4-dihydro-4-oxoquinoline-3-carboxylic acid formic acid salt (KR-10802)

1-Cyclopropyl-7-[3,7-diazabicyclo[3.3.0] oct-1(5)-en-3-yl]-6,8-difluoro-1,4-dihydro4-oxoquinoline-3-carboxylic acid (0.1 g), which was prepared in Example 11 was purged under vacuum to remove any trace of solvent and gave the title compound (0.95 g, yield 85%).

mp: 197°~200° C.(dec.)

Example 13

Preparation of 1-cyclopropyl-7-[3,7-diazabicyclo[3.3.0] oct-1(5)-en-3-yl]-6,8-difluoro-1,4-dihydro-4-oxoquinoline-3-carboxylic acid hydrochloride (KR-10777)

0.5 g of 1-cyclopropyl-7-[3,7-diazabicyclo[3.3.0] oct-1(5)-en-3-yl]-6,8-difluoro-1,4-dihydro-4-oxoquinoline-3-carboxylic acid, which was prepared in Example 11, was dissolved in conc. hydrochloric acid (10 ml) and methanol (10 ml). The insoluble portion was filtered off and the filtrate was concentrated to dryness and then washed with 50% ethanol (5 ml) and ethanol (10 ml) successively. The title compound (0.42 g, yield 77%) was obtained.

mp: 197°~201° C.(dec.)

$^1$H-NMR (D$_3$O, δ ppm): 8.69 (1H, s), 7.20 (1H, d, J=14.2 Hz), 4.52 (4H, br. s),4.20 (4H, s), 3.92 (1H, m), 1.24~1.08 (4H, m).

EXAMPLE 14

1-Cyclopropyl-7-[3,7-diazabicyclo[3.3.0] oct-1(5)-en-3-yl]-6,8-difluoro-1,4-dihydro-4-oxoquinoline-3-carboxylic acid hydrochloride (KR-10777)

0.6 g of 1-cyclopropyl-7-[3,7-diazabicyclo[3.3.0] oct-1(5)-en-3-yl]-6,8-difluoro-1,4-dihydro-4-oxoquinoline-3-carboxylic acid, which was prepared in Example 11, was dissolved in 2% acetic acid (50 ml). To this solution conc. hydrochloric acid (5 ml) and ethanol (100 ml) were added and kept in an ice bath. The precipitate was filtered as the title compound (0.4 g, yield 60%).

mp: 197°~201° C.(dec.)

EXAMPLE 15

Preparation of 1-cyclopropyl-6-fluoro-7-[7-methyl-3,7-diazabicyclo [3.3.0] oct-1(5)-en-3-yl]-4-oxo-1,8-naphthylidine-3-carboxylic acid hydrochloride (KR-10816)

To a solution of 1,8-diazabicyclo[5.4.0] undec-7-ene (DBU) in pyridine (40 ml), 7-chloro-1-cyclopropyl-6-fluoro-1,4-dihydro-4-oxo-1,8-naphthylidine-3-carboxylic acid (2.1 g) and 3,7-diazabicyclo[3.3.0] oct-1(5)-ene dihydrobromide (2 g) were added and stirred at room temperature for 1.5 hours. The produced precipitate was filtered and washed with acetonitrile (20 ml) to give 1-cyclopropyl-6-fluoro-7-[3,7-diazabicyclo[3.3.0] oct-1(5)-en-3-yl]-4-oxo-1,8-naphthylidine-3-carboxylic acid (KR-10797, 2.6 g, yield 97%). To this compound, 37% formaline (20 ml) and 98% formic acid (20 ml) were added and refluxed for 6 hours. The reagents were removed under vacuum and methanol (20 ml) and conc. hydrochloric acid (10 ml) were added and them stirred at room temperature for 30 minutes. The solvents were removed, washed with iso-propanol (50 ml) to give the title compound (2.5 g, yield 84%).

mp. 240°-245° C.(dec.).

Example 16

1-Cyclopropyl-7-[3,7-diazabicyclo[3.3.0] oct-1(5)-en-3-yl]-6-fluoro-1,4-dihydro-4-oxoquinoline-3-carboxylic acid 1-Cyclopropyl-6,7-difluoro-1,4-dihydro-4-oxoquinoline-3-carboxylic acid (4.4 g) and 3,7-diazabicyclo[3.3.0] oct-1(5)-ene dihydrobromide (4.2 g) were added to diisopropyl ethylamine (11.6 ml) in acetonitrile (120 ml) and refluxed for 7 hours. The produced precipitate was filtered, washed with acetonitrile (100 ml), water (50 ml), ethanol (50 ml) and them ethyl ether (50 ml) to give the title compound (4.2 g, yield 77%).

mp: 239°~242° C.

$^1$H-NMR (CD$_3$COOD, δ ppm): 8.57 (1H, s), 7.82 (1H, d, J=12.2 Hz), 7.12 (1H, d, J=7.4 Hz), 4.52 (4H, s), 4.20 (4H, s), 3.82 (1H, m), 1.37 (2H, m), 1.20 (2H, m).

Example 17

1-Cyclopropyl-7-[3,7-diazabicyclo[3.3.0] oct-1(5)-en-3-yl]-6-fluoro-1,4-dihydro-4-oxoquinoline-3-carboxylic acid formic acid salt (KR-10824)

1.6 g of 1-Cyclopropyl-7-[3,7-diazabicyclo [3.3.0] oct-1(5)-en-3-yl]-6-fluoro-1,4-dihydro-4-oxoquinoline-3-carboxylic acid which was prepared in Example 16, was dissolved in 98% formic acid (150 ml). The insoluble portion was removed by filtration, and the filtrate was concentrated under vacuum, washed with ethanol (30 ml) and ethyl ether (30 ml) to give the title compound (1.7 g, yield 94%).

mp: 245°~250° C. (dec.).

EXAMPLE 18

1-Cyclopropyl-7-[3,7-diazabicyclo[3.3.0] oct-1(5)-en-3-yl]-6-fluoro-1,4-dihydro-4-oxoquinoline-3-carboxylic acid hydrochloride (KR-10787)

1-Cyclopropyl-6,7-difluoro-1,4-dihydro-4-oxoquinoline-3-carboxylic acid (1.07 g), 3,7-diazabicyclo[3.3.0] oct-1(5)-ene dihydrobromide (1.08 g) and 1,8-diazabicyclo[5.4.0] undec-7-ene (DBU, 2 ml) were suspended in acetonitrile (20 ml) and refluxed for 3 hours. After cooling the reaction mixture, the produced precipitate was collected by filtration and washed with acetonitrile and methanol. The solid was dissolved in methanol (5 ml) and conc-hydrochloric acid (5 ml) and then insoluble portion was filtered off. The filtrate was concentrated under vacuum, washed with ethanol to give the title compound (0.95 g, yield 60%)

mp: 260°-263° C.

$^1$H-NMR(CDCl$_3$+CD$_3$COOD, δ ppm): 9.36 (1H, s), 7.87 (1H, d, J =12.2 Hz), 6.85 (1H, d, J=7.4 Hz), 4.50 (4H, s), 4.27 (4H, s), 3.53 (1H, m), 1.40 (2H, m), 1.27 (2H, m).

EXAMPLE 19

1-Cyclopropyl-6-fluoro-7-[7-methyl-3,7-diazabicyclo[3.3.0] oct-1(5)-en-3-yl]-1,4-dihydro-4-oxoquinoline-3-carboxylic acid hydrochloride (KR-10820)

1.5 g of 1-Cyclopropyl-7-[3,7-diazabicyclo[3.3.0] oct-1(5)-en-3-yl]-6-fluoro-1,4-dihydro-4-oxoquinoline-3-carboxylic acid which was prepared in Example 16 was dissolved in 98% formic acid (18 ml) and 37% formaline (18 ml) and refluxed for 5 hours. The excess reagents were removed under vacuum. To the product 150 ml of iso-propanol saturated with HCl gas was added and refluxed for 1 hours. The solvent was purged under vacuum, washed with iso-propanol to give the title compound (1.48 g, yield 86%).

mp: 260°~263° C.

$^1$H-NMR (D$_2$O, δ ppm): 8.27 (1H, s), 6.93 (1H, d, J =13.8 Hz), 5.58 (1H, d, J =7.3 Hz), 4.25 (2H, br, s), 3.99 (4H, s), 3.80 (2H, br, s), 3.23 (1H, m), 2.88 (3H, s), 1.12-0.89 (4H, m).

EXAMPLE 20

Preparation of
1-cyclopropyl-6,8-difluoro-7-[7-ethyl-3,7-diazabicyclo[3.3.0]
oct-1(5)-en-3-yl]-1,4-dihydro-4-oxoquinoline-3-carboxylic acid (KR-10831)

1-Cyclopropyl-6,7,8-trifluoro-1,4-dihydro-4-oxoquinoline-3-carboxylic acid (0.48 g), N-ethyl-3,7-diazabicyclo [3.3.0] oct-1(5)-ene dihydrobromide (0.57 g) and 1,8-diazabicyclo [5.4.0] undec-7-ene (DBU, 0.87 ml) were dissolved in acetonitrile (20 ml) and refluxed for 3 hours. After cooling the reaction mixture, the produced precipitate was collected by filteration and washed with acetonitrile (10 ml) and methanol (10 ml) to give the title compound (0.5 g, yield 73%)
mp: 188°~192° C.
$^1$H-NMR (CDCl$_3$ +CD$_3$COOD, δ ppm): 8.86 (1H, s), 7.86 (1H, d, J =14.2 Hz), 4.82 (2H, br, s), 4.68 (4H, s), 4.30 (2H, q, J =7.1 Hz), 3.96 (1H, m), 3.88 (2H, br, s), 1.48 (3H, t, J =7.1 Hz), 1.27 (4H, m).

EXAMPLE 21

Preparation of 7-[3,7-diazabicyclo
[3.3.0]oct-1(5)-en-3-yl]-6,8-difluoro-1-(4-fluorophenyl)-1,4-dihydro-4-oxoquinoline-3-carboxylic acid (KR-10798)

1-(4-Fluorophenyl)-6,7,8-trifluoro-1,4-dihydro-4-oxoquinoline-3-carboxylic acid (0.33 g), 3,7-diazabicyclo[3.3.0] oct-1(5)-ene dihydrobromide (0.27 g) and 1,8-diazabicyclo [5.4.0] undec-7-ene (DBU, 1 ml) were dissolved in acetonitrile (10 ml) and refluxed for 4 hours. The reaction mixture was kept overnight at room temperature and the produced precipitate was filtered, washed with acetonitrile, methanol to give the title compound (0.28 g, yield 66%).
mp: 195°~198° C.
$^1$H-NMR (CDCl$_3$+CD$_3$COOD, δ ppm): 8.55 (1H, s), 7.94 (1H, d, J =14.3 Hz), 7.43 (2H, m), 7.25 (2H, m), 4.55 (4H, s), 4.15 (4H, s).

Example 22

Preparation of 7-[3,7-diazabicyclo [3.3.0]
oct-1(5)-en-3-yl]-1-(2,4-difluorophenyl)-6,8-difluoro-1,4-dihydro-4-oxoquinoline-3-carboxylic acid (KR-10817)

1-(2,4-Difluorophenyl)-6,7,8-trifluoro-1,4-dihydro-4-oxoquinoline-3-carboxylic acid (1.07 g), 3,7-diazabicyclo [3.3.0] oct-1(5)-ene dihydrobromide (1 g) and 1,8-diazabicyclo [5.4.0] undec-7-ene (DBU, 2 ml) were dissolved in acetonitrile (30 ml) and refluxed for 7 hours. The reaction mixture was kept overnight at room temperature and the produced precipitate was filtered and then suspended in methanol (10 ml) and sonicated for 30 minutes. The insoluble product was collected by filtration to give the title compound (1 g, yield 74%).
mp: 231°~235° C. (dec.).
$^1$H-NMR (CDCl$_3$+CD$_3$COOD, δ ppm): 8.60 (1H, s), 7.96 (1H, d, J=14.2 Hz), 7.39~7.23 (3H, m), 4.51 (4H, s), 4.14 (4H, s).

Example 23

Preparation of 1-ethyl-7-[3,7-diazabicyclo [3.3.0] oct-1(5)-en-3-yl]-6-fluoro-1,4-dihydro-4-oxoquinoline-3-carboxylic acid 7-Chloro-1-ethyl-6-flroro-1,4-dihydro-4-oxoquinoline-3-carboxylic acid (0.27 g), 3,7-diazabicyclo [3.3.0] oct-1(5)-ene dihydrobromide (0.31 g), 1,8-diazabicyclo [5.4.0] undec-7-ene (DBU, 0.52 ml) in acetonitrile (10 ml) was refluxed for 7 hours. The reaction mixture was kept overnight at room temperature and the produced precipitate was filtered, washed with acetonitrile, water and dried in vacuum to yield the title compound (0.25 g, yield 72%)
mp: 229°~232° C. (dec.).
$^1$H-NMR (CDCl$_3$+CD$_3$COOD, δ ppm): 8.55 (1H, s), 7.85 (1H, d, J=12.3 Hz), 7.14 (1H, d, J=7.3 Hz), 4.54 (4H, s), 4.36 (2H, q, J=7.1 Hz), 4.23 (4H, s), 1.46 (3H, t, J=7.1 Hz).

Example 24

Preparation of 1-tert-butyl-7-[3,7-diazabicylo [3.3.0] oct-1(5)-en-3-yl]-6,8-difluoro-1,4-dihydro-4-oxoquinoline-3-carboxylic acid 1-tert-Butyl-6,7,8-trifluoro-1,4-dihydro-4-oxoquinoline-3-carboxylic acid (0.32 g), 3,7-diazabicyclo-[3.3.0] oct-1(5)-ene dihydrobromide (0.3 g) and 1,8-diazabicyclo [5.4.0] undec-7-ene (DBU, 0.55 ml) in acetonitrile (12 ml) was refluxed for 5 hours. The produced precipitate was collected by filtration, washed with acetonitrile and methanol to give the title compound (0.38 g, yield 92%)
mp: 265°~268° C.
$^1$H-NMR (CDCl$_3$+CD$_3$COOD, δ ppm): 8.57 (1H, s), 8.02 (1H, d, J=14.2 Hz), 4.50 (4H, s), 4.17 (4H, s), 1.87 (9H, s).

Example 25

Preparation of
1-cyclopropyl-6,8-difluoro-7-[7-ethyl-3,7-diazabicyclo [3.3.0]
oct-1(5)-en-3-yl]-1,4-dihydro-4-oxoquinoline-3-carboxylic acid To a solution of 1-cyclopropyl 6,8-difluoro-7-[3,7-diazabicyclo [3.3.0]-oct-1(5)-en-3-yl]-1,4-dihydro-4-oxoquinoline-3-carboxyl-ic acid (0.37 g) in dimethyl formamide (30 ml), which was prepared in Example 11, ethyliodide (0.17 g) and potassium carbonate (powder, 1 g) were added and stirred at room temperature for 24 hours. To the reaction mixture, water (100 ml) was added and the precipitate was filtered. The filter cake was purified by silica gel column chromatography (CHCl$_3$:methanol:acetic acid=6:3:1) to give the title compound (0.21 g, yield 52%).
mp: 188°~192° C.

Example 26

Preparation of
1-cyclopropyl-6,8-difluoro-7-[7-methyl-3,7-diazabicyclo[3.3.0
]oct-1(5)-en-3-yl]-1,4-dihydro-4-oxoquinoline-3-carboxylic acid (KR 10845)

1-Cyclopropyl-6,7,8-trifluoro-1,4-dihydro-4-oxoquinoline-3-carboxylic acid (0.42 g), 3-methyl-3,7-diazabicyclo[3.3.0]oct-1(5)-ene dihydrobromide (0.47 g) and 1,8-diazabicyclo[5.4.0]undec-7-ene (DBU, 0.63 g) were dissolved in acetonitrile (20 ml) and refluxed for 7 hours. The reaction mixture was kept at room temperature overnight and then the produced precipitate was filtered, washed with acetonitrile and methanol to give the title compound 0.36 g (yield 62%).

¹H-NMR (CDCl₃+CD₃COOD, δ ppm): 8.84 (1H, s), 7.87 (1H, dd, J=14.3, 1.8 Hz), 4.68 (4H, s), 4.32 (4H ,s), 4.01 (1H, m), 3.09 (3H ,s), 1.28 (2H, m), 1.19 (2H, m).

Example 27

Preparation of 1-cyclopropyl-6,8-difluoro-7-[7-methyl-3,7-diazabicyclo[3.3.0]oct-1(5)-en-3-yl]-1,4-dihydro-4-oxoquinoline-3-carboxylic acid hydrochloride (KR 10755)

0.3 g of 1-cyclopropyl-6,8-difluoro-7-[7-methyl-3,7-diazabicyclo[3.3.0]oct-1(5)-en-3-yl]-1,4-dihydro-4-oxoquinoline-3-carboxylic acid which was prepared in Ex. 26 was dissolved in 10 ml of 5% acetic acid in water and then 35% hydrochloric acid 2 ml and 20 ml of ethanol were added. The mixture was kept in a ice-water bath for 1 hour and then the resulting precipitate was filtered, washed with ethyl-ether and dried in vacuo to give 0.25 g of the title compound (yield 78%)
mp: 210°~213° C. (dec.).

Example 28

Preparation of 6,8-difluoro-7-[3,7-diazabicyclo[3.3.0]oct-1(5)-en-3-yl]-1-(2-fluoroethyl)-1,4-dihydro-4-oxoquinoline-3-carboxylic acid 1-(2-Fluoroethyl)-6,7,8-trifluoro-1,4-dihydro-4-oxoquinoline-3-carboxylic acid (0.29 g), 3,7-diazabicyclo [3.3.0]oct-1(5)-ene dihydrobromide (0.33 g) and 1,8-diazabicyclo [5.4.0]undec-7-ene (DBU, 0.46 g) were dissolved in acetonitrile (15 ml) and refluxed for 3 hours. The reaction mixture was kept at room temperature overnight and the precipitate was collected by filtration, washed with acetonitrile and methanol to give the title compound (0.29 g, yield 76%).
mp: 241°~245° C. (dec.).

¹H-NMR (CDCl₃+CD₃COOD, δ ppm): 8.86 (1H, s), 7.88 (1H, dd, J=14.2, 1.8 Hz), 4.68 (4H, s), 4.50 (1H, t, J=7.8 Hz), 4.23 (4H, s), 3.46 (1H, t, J=7.8 Hz), 3.05 (1H, t, J=7.8 Hz), 2.91 (1H, t, J=7.8 Hz).

Example 29

Preparation of 7-[7-methyl-3,7-diazabicyclo[3.3.0]oct-1(5)-en-3-yl]-1-(2,4-difluorophenyl)-6,8-difluoro-1,4-dihydro-4-oxoquinoline-3-carboxylic acid hydrochloride (KR-10819).

7-[3,7-Diazabicyclo[3.3.0]oct-1(5)-en-3-yl]-1-(2,4-difluorophenyl)-6,8-difluoro-1,4-dihydro-4-oxoquinoline-3-carboxylic acid prepared in Example 22 (445 mg) was dissolved in 10 ml of 98% formic acid and 2 ml of 37% formaline was added. The mixture was refluxed for 4 hours and the excess reagents were removed under reduced pressure. The resulting solid was dissolved in 5 ml of water and the insoluble portion was removed by filteration. To the filtrate 4N-NaOH was added to make pH 8. The precipitate was filtered and dried under vacuum and then the solid material was dissolved in dichloromethane (5 ml) and ethanol (1 ml). Dried HCl gas was introduced to produce precipitate. The precipitate was filtered and washed with ethyl ether to give the title compound (404 mg, yield 88%).
mp: 247°–251° C. (dec.).

¹H-NMR (CDCl₃+CD₃OD, δ ppm): 8.57 (1H, s), 7.94 (1H, d, J =14.1 Hz), 7.42(1H, m), 7.17 (2H, m), 4.67 (4H, s), 4.10 (4H, s), 3.20 (3H, s).

Quinolone compounds prepared in the above Examples, were tested for their antibacterial activities by the agar dilution test method. The results are shown in Table I and Table II.

The quinolone compounds of the general formula I according to the present invention have much better antibacterial activities against Gram positive bacteria than the existing quinolone antibacterial agents, as e.g. ciprofloxacin and ofloxacin, and have a similar or better antibacterial activity against Gram negative bacteria than ciprofloxacin or ofloxacin. These compounds have also an excellent antibacterial activity against Pseudomonas aeruginosa, they are superior in their antibacterial activity to existing quinolone antibacterial agents against the methicilline resistant Staphylococcus aureus (Table II) and also have an excellent effect in antibacterial tests against bacteria resistant to quinolones already used.

TABLE I

The in vitro antibacterial activity of quinolones. Minimum inhibition concentration (μg/ml)

| No. | KR-10679 | KR-10777 | KR-10755 | KR-10758 | KR-10747 | KR-10797 | KR-10820 | KR-10798 | KR-10819 | Ofloxacin | Ciprofloxacin |
|-----|----------|----------|----------|----------|----------|----------|----------|----------|----------|-----------|---------------|
| 1   | 0.098    | 0.098    | 0.195    | 3.125    | 0.391    | 0.391    | 0.195    | 3.125    | 25       | 3.125     | 3.125         |
| 2   | 0.049    | 0.025    | 0.195    | 0.781    | 0.098    | 0.391    | 0.098    | 0.781    | 12.5     | 1.563     | 0.781         |
| 3   | 0.049    | 0.025    | 0.195    | 0.781    | 0.195    | 0.781    | 0.195    | 0.25     | 100      | 1.563     | 0.781         |
| 4   | 0.007    | 0.007    | 0.025    | 0.195    | 0.025    | 0.049    | 0.013    | 0.195    | 1.563    | 0.195     | 0.195         |
| 5   | 0.025    | 0.025    | 0.025    | 0.781    | 0.025    | 0.098    | 0.013    | 0.195    | 1.563    | 0.391     | 0.781         |
| 6   | 0.013    | 0.013    | 0.025    | 0.781    | 0.025    | 0.098    | 0.013    | 0.195    | 1.563    | 0.391     | 0.781         |
| 7   | <0.002   | <0.002   | 0.004    | 0.025    | <0.002   | 0.007    | 0.013    | 0.049    | 0.391    | 0.013     | <0.002        |
| 8   | 0.098    | 0.098    | 0.195    | 0.781    | 0.195    | 1.560    | 0.781    | 0.391    | 1.563    | 0.391     | 0.098         |
| 9   | 0.013    | 0.013    | 0.025    | 0.195    | 0.049    | 0.195    | 0.098    | 0.781    | 1.563    | 0.195     | 0.098         |
| 10  | <0.002   | <0.002   | 0.007    | 0.098    | 0.013    | 0.013    | 0.013    | 0.195    | 1.563    | 0.049     | <0.002        |
| 11  | 0.004    | <0.002   | 0.007    | 0.098    | 0.013    | 0.013    | 0.013    | 0.098    | 1.563    | 0.049     | <0.002        |
| 12  | 0.391    | 0.195    | 0.781    | 3.125    | 0.781    | 0.781    | 0.781    | 3.125    | 100      | 1.563     | 0.391         |
| 13  | 0.391    | 0.195    | 0.781    | 1.563    | 0.391    | 0.781    | 0.781    | 1.563    | 50       | 0.781     | 0.098         |
| 14  | 0.391    | 0.195    | 0.781    | 3.125    | 0.781    | 0.781    | 0.781    | 3.125    | 50       | 1.563     | 0.195         |
| 15  | 0.049    | 0.013    | 0.049    | 0.781    | 0.391    | 0.098    | 0.098    | 3.125    | 6.25     | 0.195     | 0.049         |
| 16  | 0.004    | <0.002   | 0.013    | 0.098    | 0.004    | 0.025    | 0.025    | 0.098    | 1.563    | 0.025     | 0.007         |
| 17  | <0.002   | <0.002   | <0.002   | 0.098    | 0.013    | <0.002   | <0.002   | 0.098    | 1.563    | 0.013     | 0.004         |
| 18  | 0.004    | 0.007    | 0.013    | 0.195    | 0.025    | 0.025    | 0.025    | 0.098    | 3.125    | 0.049     | 0.004         |
| 19  | 0.007    | 0.004    | 0.004    | 0.195    | 0.391    | 0.013    | 0.013    | 0.195    | 1.563    | 0.049     | 0.004         |

TABLE I-continued

The in vitro antibacterial activity of quinolones. Minimum inhibition concentration (μg/ml)

| No. | KR-10679 | KR-10777 | KR-10755 | KR-10758 | KR-10747 | KR-10797 | KR-10820 | KR-10798 | KR-10819 | Ofloxacin | Ciprofloxacin |
|---|---|---|---|---|---|---|---|---|---|---|---|
| 20 | <0.002 | <0.002 | <0.002 | 0.049 | <0.002 | 0.013 | 0.004 | 0.049 | 0.391 | 0.013 | <0.002 |

1 *Streptococcus pyogenes* 308
2 *Streptococcus pyogenes* 77
3 *Streptococcus faecium* MD 8b
4 *Staphylococcus aureus* SG 511
5 *Staphylococcus aureus* 285
6 *Staphylococcus aureus* 503
7 *Escherichia coli* O 55
8 *Escherichia coli* DC 0
9 *Escherichia coli* DC 2
10 *Escherichia coli* TEM
11 *Escherichia coli* 1507E
12 *Pseudomonas aeruginosa* 9027
13 *Pseudomonas aeruginosa* 1592E
14 *Pseudomonas aeruginosa* 1771
15 *Pseudomonas aeruginosa* 1771M
16 *Salmonella typhimurium*
17 *Klebsiella aerogenes* 1082E
18 *Klebsiella aerogenes* 1522E
19 *Enterobacter cloacae* P 99
20 *Enterobacter cloacae* 1321E

TABLE II

The in vitro antibacterial activity of quinolones against methicilline resistant strains

| | | Minimum inhibition concentration (μg/ml) | | |
|---|---|---|---|---|
| No. | Methicillin resistant strains | KR-10679 | KR-10747 | Ofloxacin |
| 1 | *Staphylococcus aureus* 88 E | 0.195 | 0.049 | 0.391 |
| 2 | *Staphylococcus aureus* 121 E | 0.098 | 0.049 | 0.195 |
| 3 | *Staphylococcus aureus* 208 E | 0.098 | 0.098 | 0.391 |
| 4 | *Staphylococcus aureus* 256 E | 0.098 | 0.049 | 0.195 |
| 5 | *Staphylococcus aureus* 690 E | 0.049 | 0.025 | 0.195 |
| 6 | *Staphylococcus aureus* 692 E | 0.049 | 0.013 | 0.098 |
| 7 | *Staphylococcus aureus* 693 E | 0.049 | 0.025 | 0.195 |
| 8 | *Staphylococcus aureus* 694 E | 0.098 | 0.049 | 0.195 |
| 9 | *Staphylococcus aureus* 695 E | 0.098 | 0.025 | 0.195 |
| 10 | *Staphylococcus aureus* 697 E | 0.025 | 0.025 | 0.098 |
| 11 | *Staphylococcus aureus* 701 E | 0.098 | 0.098 | 0.195 |
| 12 | *Staphylococcus aureus* 703 E | 0.098 | 0.049 | 0.195 |
| 13 | *Staphylococcus aureus* 705 E | 0.098 | 0.098 | 0.391 |
| 14 | *Staphylococcus aureus* 706 E | 0.049 | 0.049 | 0.195 |
| 15 | *Staphylococcus aureus* 707 E | 0.098 | 0.098 | 0.195 |
| 16 | *Staphylococcus aureus* 708 E | 0.025 | 0.013 | 0.098 |
| 17 | *Staphylococcus aureus* 711 E | 0.049 | 0.013 | 0.098 |
| 18 | *Staphylococcus aureus* 714 E | 0.049 | 0.025 | 0.195 |
| 19 | *Staphylococcus aureus* 725 E | 0.098 | 0.049 | 0.195 |

We claim:

1. A quinolone or naphthyridone compound of the formula I in which
X represents C—H, C—F or N,
Z represents hydrogen, halogen or amino,
$R_1$ represents hydrogen or a pharmaceutically acceptable cation,
$R_2$ represents alkyl, halogenated alkyl or hydroxyalkyl having 1 to 4 carbon atoms, vinyl, cycloalkyl having 3 to 6 carbon atoms or fluorophenyl,
$R_3$ represents hydrogen, lower alkyl or formyl,
m is an integer of 1 to 3, and
n is 1 or 2,
and, in case $R_1$ is hydrogen, pharmaceutically acceptable acid addition salts and the hydrates thereof.

2. A pharmaceutical composition active against bacterial infections, which contains an effective amount of a quinolone of the formula I or a pharmaceutically acceptable salt or hydrate thereof.

3. Method for treating bacterial infections of warmblooded animals which comprises administering an effective amount of a quinolone of the formula I or a pharmaceutically acceptable salt or hydrate thereof or a pharmaceutical composition containing such compound.